United States Patent [19]

Rosenberg et al.

[11] Patent Number: 4,606,915

[45] Date of Patent: Aug. 19, 1986

[54] ANTIPERSPIRANT COMBINATION CONTAINING AN ALUMINUM HALOHYDRATE AND A STANNIC HALIDE

[75] Inventors: Allan H. Rosenberg, Randolph; Leonard Weintraub, Millburn, both of N.J.

[73] Assignee: Bristol-Myers Company, New York, N.Y.

[21] Appl. No.: 256,649

[22] Filed: Apr. 23, 1981

[51] Int. Cl.[4] .......................... A61K 7/34; A61K 7/38

[52] U.S. Cl. .............................. 424/68; 424/DIG. 5; 556/27

[58] Field of Search ..................... 424/DIG. 5, 65, 68, 424/69; 260/429.7, 448

[56] References Cited

U.S. PATENT DOCUMENTS

| | | | |
|---|---|---|---|
| 2,145,583 | 1/1939 | Carlson | 424/67 |
| 2,236,387 | 3/1941 | Wallace, Jr. | 424/67 |
| 2,294,140 | 8/1942 | Taylor | 424/67 |
| 3,555,146 | 1/1971 | Jones et al. | 424/65 |
| 3,721,693 | 3/1973 | Fein et al. | 424/65 |
| 3,970,748 | 7/1976 | Mecca | 260/448 R |
| 4,237,061 | 2/1980 | Johnson | 260/429.7 |

FOREIGN PATENT DOCUMENTS

| | | | |
|---|---|---|---|
| 1452532 | 10/1976 | United Kingdom | 424/68 |

*Primary Examiner*—Dale R. Ore
*Attorney, Agent, or Firm*—Gabriel P. Katona

[57] ABSTRACT

An antiperspirant combination containing an aluminum halohydrate and a stannic halide and also preferably containing a neutral amino acid. Material in powder form or incorporated in liquid or solid vehicle is useful in inhibiting perspiration when applied to the skin of a subject.

16 Claims, No Drawings

ANTIPERSPIRANT COMBINATION CONTAINING AN ALUMINUM HALOHYDRATE AND A STANNIC HALIDE

This invention relates to new antiperspirant combinations which are highly effective and have a low irritation potential for skin. Mcre particularly, it concerns antiperspirant combinations containing a stannic halide, an aluminum halohydrate as active antiperspirant ingredients and which may also contain a neutral amino acid.

There have been some suggestions in the prior art for using tin salts such as tin chloride in a shaving cream preparation which will tend to stop or deodorize perspiration. Such compositions are described in U.S. Pat. No. 2,145,583. Similarly, there has been some vague teaching for using metallic salts of mineral acids e.g. tin salts of hydrochloric acid to inhibit perspiration (see U.S. Pat. No. 2,236,387). To reduce the corrosive action of these materials, the patentee recommends the use of, among other things, amino acids e.g. glycine. Compositions of this character, however, left much to be desired both from the point of view of irritation potential and/or activity.

It has now been found that highly effective antiperspirant combinations of low irritation potential for skin can be provided by mixing a stannic halide with an aluminum halohydrate preferably together with a neutral amino acid.

One of the mechanisms believed to contribute to the antiperspirant effectiveness of metal salts is their ability to form obstructive hydroxide gels in the sweat ducts. Metal salts are believed to hydrolyze to form acidic solutions that diffuse into the sweat ducts and then form insoluble hydroxide on being neutralized by the sweat present in the ducts. Their ability to form hydroxide plugs (as a function of the sweat pH), the type of plug formed (i.e. gelatinous or crystalline) and the depth of penetration into the sweat duct all appear to contribute to the antiperspirant activity of metal salts.

It has been found by in vitro diffusion studies that antiperspirant conbinations of the present invention in solution have the properties that are consistent with effective antiperspirant activity. These solutions diffuse quite deeply into capillary tubes before precipitation occurs. Furthermore, gelatinous precipitates are formed at relatively low pH (5.0).

Moreover, animal toxicity data indicates that the combinations embodied in this invention are non-toxic and non-irritating. This has been demonstrated in animal studies at concentrations in the range of from 16 to 48%.

It is accordingly an object of the present invention to provide an effective antiperspirant combination containing an aluminum halohydrate and a stannic halide that may also contain a neutral amino acid and that is low in irritation potential for skin.

Other and more detailed objects of this invention will be apparent from the following description and claims.

The antiperspirant combinations of the present invention correspond to the empirical composition:

$$[Al_2(OH)_5X.nH_2O]_a.[SnY_4.n'H_2O]_b.\ [\text{Neutral Amino Acid}]_c \quad (I)$$

wherein:

(1) X and Y are halogen, preferably chlorine;

(2) n and n' are numbers from 0 to 6;

(3) the ratio by weight of a/b is from about 0.3 to about 1.8; and (4) the ratio by weight of c/b is from 0 to about 1.3.

This corresponds to a mole ratio of Al/Sn of from about 1 to about 6 and a mole ratio of neutral amino acid/Sn of from 0 to about 6. The preferred neutral amino acid is glycine.

The incorporation of a neutral amino acid and particularly glycine in the present antiperspirant combinations, although it is an optional feature is highly desirable. Aluminum chlorohydrate, for example, when added to $SnCl_4.5H_2O$ solution reduces the acidity of the solution and within certain ranges of concentration provide solutions that are stable with respect to gellation. This range of stability can be increased by the addition of a neutral amino acid such as glycine.

Two antiperspirant combinations falling within the above definition have been found to be particularly suitable. One combination identified hereinafter as SnAG A corresponds to Formula I above in which glycine is the amino acid, chloride is the halogen, n=2, n'=5, and is characterized by the following weight ratios:

$$a/b=1.11;\ c/b=0.22$$

A second combination identified hereinafter as SnAG B corresponds to Formula I above in which glycine is the amino acid, chloride is the halogen, n=2, n'=5, and is characterized by the following weight ratios:

$$a/b=1.11;\ c/b=0.43$$

The antiperspirant combinations of the present invention are prepared by mixing the aluminum halohydrate, the stannic halide and, when employed, the amino acid in solution. It is not clear whether a true molecular complex is formed in the process or whether a simple mixture is formed. Consequently, as used herein, the term antiperspirant combination is intended to include true molecular complexes of the various ingredients or mere mixtures thereof.

The antiperspirant combinations of the present invention are generally prepared by forming a solution, usually an aqueous solution, of the ingredients in the appropriate ratios. The solution is then dried to remove the solvent and form a dry powder. Various processes are known in the art to obtain the requisite dried product. These include evaporation under vacuum, spray drying, etc. The dried powder can then be used to formulate various products.

However, the solution of the antiperspirant combination described above can be used as such as an antiperspirant agent without first drying the solution to form a powder. Furthermore, when the final product is to take the form of a solution containing the solvent used to prepare the combination or to form an emulsion in which the solution of the antiperspirant combination forms all or part of a phase of said emulsion, the solution of the antiperspirant combination may also be used directly i.e. without first going through a drying step.

The antiperspirant combinations of the present invention may be used in a variety of dosage forms. Thus, they may be used in the form of simple solutions in solvents in which they are sufficiently soluble e.g. water, alcohol, hydro-alcoholic solvents. These may be dispensed by means of the conventional roll-on applicators widely used in this art or other types of applicators suitable for dispensing solutions of this character. These solutions may also be dispensed in the form of pads which have been saturated with these solutions.

The antiperspirant combination of the present invention may be used in the form of a suspension type product. In this case, the dried product could be distributed in a vehicle in which it is suspendable but not soluble. These will usually be hydrophobic vehicles which can be exemplified by such materials as silicones such as cyclomethicone and dimethicone, esters such as isopropyl myristate or dibutyl phthalate, long chain fatty alcohols such as stearyl alcohol and glycols such as propylene glycol, etc. These too could be dispensed in the form of a roll-on applicator.

In a similar fashion, the antiperspirant combinations of this invention, in form of a solution, could be formulated into emulsion type products to be dispensed from roll-on type applicators or aerosol dispensers or may be incorporated in creams, ointments. In the dry form, these materials can be included as the active ingredients in antiperspirant stick products or dispensed as a powder.

The quantity of the present antiperspirant combination, which may or may not contain the amino acid, that will be contained in products in accordance with the present invention will vary depending on the particular dosage form and the degree of activity required. Usually, however, on a dry basis it will comprise from about 3% to about 50% by weight based on the total weight of the composition and preferably, from about 15% to about 30% on the same weight basis.

The following Examples are given to further illustrate the present invention. It is understood, however, that the invention is not limited thereto.

EXAMPLE 1

Preparation of SnAG A Powder

In a glass beaker, 185 g. of glycine is added to 1910 g. of a 50% aqueous solution of aluminum chlorhydrate. The mixture is stirred by means of a magnetic stirrer until a clear solution is obtained. (This solution is called Solution I).

In another glass beaker, 860 g. of stannic chloride pentahydrate is added to 1209 g. of deionized water. The mixture is heated to approximately 50° C. (by means of hot plate) and stirred until a clear solution is obtained. (This solution is called Solution II).

Solution I is slowly added to Solution II with stirring until a uniform, clear solution is obtained. SnAG A solid is obtained from the resultant aqueous SnAG A solution by evaporating the solution under vacuum (using a one stage vacuum pump at less than 10 torr) at 70° C. by means of a Buchi Roto-Vapor. The resultant SnAG A solid is ground in a mortar and pestle and then redried for one hour at 70° C. in the Roto-Vapor. The redried solid is then re-ground in a mortar and pestle and stored.

In an alternative procedure, the drying operation can be accomplished by spray drying the clear solution obtained from mixing Solution I and Solution II above. In this procedure, a Niro Atomizer is employed in which the inlet temperature is maintained at 200° C. and the outlet temperature is maintained in the range of about 122° C. to 130° C.

A 20% aqueous solution of the solid obtained from the above processes has a pH of 3.3; whereas, a 16% solution had a pH of 3.5.

EXAMPLE 2

Preparation of SnAG B Powder

Using the same procedure outlined above, SnAG B powder was produced. However, in this instance, the following quantities of starting materials are employed:

Glycine: 233 g.

Aluminum Chlorhydrate (50% solution): 1200 g.

Stannic Chloride:

Pentahydrate: 540 g.

Deionized water: 900 g.

A 20% aqueous solution of the solid obtained by this process had a pH of 3.5; whereas, a 16% solution had a pH of 3.7.

The following Examples 3, 3A, 4 and 5 are aqueous compositions of SnAG A and SnAG B that are useful as antiperspirants:

EXAMPLE 3

Formula 1976

| Ingredients | % by Wt. |
|---|---|
| SnAG A (powder) | 24.00 |
| Deionized water | 76.00 |

Appearance: Clear solution

Color: water white to slightly yellow pH: 3.1±0.5

Total SnAG A in Formula: 24.0±2.4%

EXAMPLE 3A

A composition like Formula 1976 is prepared, excepting that 12% SnAG A powder is used with 88% deionized water.

EXAMPLE 4

Formula 1977

| Ingredients | % by Wt. |
|---|---|
| SnAG B (powder) | 24.00 |
| Deionized water | 76.00 |

Appearance: Clear solution

Color: Water white to slightly yellow pH: 3.3±0.5

Total SnAG B in Formula: 24.0±2.4%

EXAMPLE 5

Formula 1978

| Ingredients | % by Wt. |
|---|---|
| SnAG A (powder) | 48.00 |
| Deionized water | 52.00 |

Appearance: Clear to slightly hazy solution

Color: Water white to slightly yellow pH: 2.3±0.5

Total SnAG A in Formula: 48.0±4.8%

The following Examples are given in tabular form (Table I). These illustrate a variety of aqueous compositions containing varying amounts of the ingredients contained in the antiperspirant combination of the present invention. The various mole ratios of materials are specified in the Table.

TABLE I

| SnAG Compositions | | | | | | | | | |
|---|---|---|---|---|---|---|---|---|---|
| | Component Wgt. (g) | | | | Weight | | Mole Ratios | | |
| Compound | ACH (50%) | $SnCl_4.5H_2O$ | Glycine | $H_2O$ | % Solids | pH | Al/Sn | Al/Glycine | Glycine/Sn |
| SnAG III | 100 | 30.5 | 13.3 | 100 | 38 | 3.1 | 5.5 | 2.7 | 2.0 |
| SnAG I | 200 | 61 | 26.7 | 100 | 48 | 2.7 | 5.5 | 2.7 | 2.0 |
| SnAG VIII | 100 | 30.5 | 6.6 | 44.4 | 48 | 2.4 | 5.5 | 5.5 | 1.0 |
| SnAG V | 100 | 45 | 19.4 | 75 | 48 | 2.7 | 3.7 | 1.8 | 2.0 |
| SnAG VI | 100 | 45 | 9.7 | 63.3 | 48 | 2.4 | 3.7 | 3.7 | 1.0 |
| SnAG IV[a] | 100 | 15.3 | 13.3 | 100 | 34 | 3.5 | 10.9 | 2.7 | 4.0 |
| SnAG A | 1910 | 859.5 | 185.3 | 1209 | 48 | 2.4 | 3.7 | 3.7 | 1.0 |
| SnAG B | 1200 | 540 | 232.8 | 900 | 48 | 2.7 | 3.7 | 1.8 | 2.0 |

[a]= SnAG IV Solution Slightly Hazy
Solid SnAG I, VI, A and B are obtained by evaporating from solution.
Solids are off-white, granular and quite hygroscopic.
pH of 20% and 16% solutions of solid A and B are 3.3, 3.5, 3.7 respectively.

EXAMPLE 6

| SnAG Suspension Roll-On 1944-3 | |
|---|---|
| Ingredients | % (w/w) |
| Bentone 38 | 2.50 |
| Anhydrous Alcohol, SD-40 | 2.00 |
| SnAG A Powder | 24.00 |
| Cyclomethicone 7158 | 71.30 |
| Perfume | 0.20 |
| | 100.00 |

EXAMPLE 7

| SnAG Roll-On 1944-4 | |
|---|---|
| Ingredients | % (w/w) |
| Polyoxypropylene fatty alcohol ethers, E-SP | 4.00 |
| Polyoxyethylene(2)stearyl ether | 2.90 |
| Polyoxyethylene(20)stearyl ether | 1.10 |
| Butylated hydroxytoluene | 0.05 |
| Disodium edetate, dihydrate | 0.10 |
| Deionized water | 67.35 |
| SnAG B powder | 24.00 |
| Perfume | 0.30 |
| Color | 0.20 |
| | 100.00 |

EXAMPLE 8

| SnAG Solid Stick 1944-5 | |
|---|---|
| Ingredients | % (w/w) |
| Stearyl alcohol | 10.00 |
| Hydrogenated castor oil MP-80 | 3.00 |
| Paraffin Wax FT 300 | 3.00 |
| Butylated hydroxytoluene | 0.05 |
| Cyclomethicone 7158 | 52.75 |
| Talc 5251 | 7.00 |
| SnAG A powder | 24.00 |
| Perfume | 0.20 |
| | 100.00 |

Precipitation Studies

SnAG solutions at concentrations of 3.8% and 16% were diffused into glass capillaries containing a buffer solution at pH 5.0 at room temperature. The capillaries were 2.5 inches long with a 0.5 mm I.D. The buffer pH was chosen to represent the low pH range of human sweat. The capillaries were filled with buffer solution and then placed in beakers containing SnAG solutions. Time to form precipitate, distance of precipitate from capillary tip and any other visual changes were recorded. Distance of precipitate from capillary tip was measured with a cathetometer. A high intensity lamp was used for illumination.

The results of these tests are summarized in Table II below:

TABLE II

| Solution | Time to Form Precipitate (min.) | Distance of Precipitate from Capillary Tip (mm.) |
|---|---|---|
| 16% SnAG I | 1 | 8.8 |
| 3.8% SnAG I | Immediate | 7.5 |
| 16% SnAG VI | 1 | 10.7 |
| 3.8% SnAG VI | Immediate | 7.8 |

In contrast to the results obtained in these tests, aluminum chlorohydrate (ACH) solutions did not precipitate at pH 5 and below. Zirconium aluminum chlorohydrate glycine (ZAG) solutions precipitated at pH 5 but did not diffuse beyond the capillary tip.

Although the invention has been described with reference to specific forms thereof, it will be understood that many changes and modifications may be made without departing from the spirit of this invention.

What is claimed is:

1. An antiperspirant combination corresponding to the empirical composition:

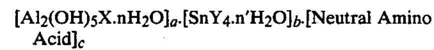

$$[Al_2(OH)_5X.nH_2O]_a.[SnY_4.n'H_2O]_b.[\text{Neutral Amino Acid}]_c$$

wherein:

(a) X and Y are halogen;

(b) n and n' are numbers from 0 to 6;

(c) the ratio by weight of a/b is from about 0.3 to about 1.8; and (d) the ratio by weight of c/b is from 0 to about 1.3.

2. An antiperspirant combination according to claim 1 corresponding to the empirical composition:

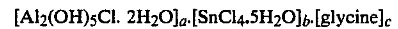

$$[Al_2(OH)_5Cl.\ 2H_2O]_a.[SnCl_4.5H_2O]_b.[\text{glycine}]_c$$

3. An antiperspirant combination according to claim 2 in the form of a dry powder.

4. An antiperspirant combination according to claim 2 contained in a liquid vehicle.

5. An antiperspirant combination according to claim 4 wherein said liquid vehicle is an aqueous vehicle.

6. An antiperspirant combination according to claim 2 contained in an antiperspirant stick vehicle.

7. An antiperspirant combination according to claim 2 in which the weight ratio of a/b is about 1.11 and the weight ratio of c/b is about 0.22.

8. An antiperspirant combination according to claim 2 in which the weight ratio of a/b is about 1.11 and the weight ratio of c/b is about 0.43.

9. An antiperspirant composition comprising a vehicle having incorporated therein from about 3% to about 50% by weight based on the total weight of said composition of the antiperspirant combination defined in claims 1, 2, 3, 7 or 8.

10. A composition according to claim 9 wherein said vehicle is a liquid vehicle.

11. A composition according to claim 10 wherein said liquid vehicle is an aqueous vehicle.

12. An antiperspirant composition comprising a vehicle having incorporated therein from about 15% to about 30% by weight based on the total weight of said composition of the antiperspirant combination defined in claims 1, 2, 3, 7 or 8.

13. A composition according to claim 12 wherein said vehicle is a liquid vehicle.

14. A composition according to claim 13 wherein said liquid vehicle is an aqueous vehicle.

15. A composition according to claim 12 wherein said vehicle is an antiperspirant stick vehicle.

16. A process for inhibiting perspiration in a subject which comprises applying to the skin of such subject an effective antiperspirant quantity of the compositions defined in claims 1, 2, 3, 4, 5, 6, 7, 8, 9, 10, 11, 12, 13, 14 or 15.

* * * * *